United States Patent [19]

Hilpert

[11] Patent Number: 5,523,463
[45] Date of Patent: Jun. 4, 1996

[54] METHOD OF PRODUCING HALOGENATED AND ALPHA-AMINOALCHOHOLS

[75] Inventor: Hans Hilpert, Reinach, Switzerland

[73] Assignee: Hoffmann-La Roche Inc., Nutley, N.J.

[21] Appl. No.: 517,887

[22] Filed: Aug. 21, 1995

[30] Foreign Application Priority Data

Sep. 23, 1994 [CH] Switzerland ............... 2905/94
Dec. 9, 1994 [CH] Switzerland ............... 3737/94

[51] Int. Cl.⁶ .................................... C07C 261/00
[52] U.S. Cl. ................ 560/137; 560/148; 560/161; 564/186; 564/224
[58] Field of Search ..................... 560/137, 148, 560/161; 564/186, 224

[56] References Cited

U.S. PATENT DOCUMENTS 5,157,041 10/1992 Handa et al. .
5,196,438 3/1993 Martin et al. .
5,430,041 7/1995 Martin et al. .
5,451,678 9/1995 Parkes et al. .
5,455,353 10/1995 Hilpert .

*Primary Examiner*—José G. Dees
*Assistant Examiner*—Samuel Bark
*Attorney, Agent, or Firm*—Gerge M. Gould; William H. Epstein; Patricia S. Rocha-Tramaloni

[57] ABSTRACT

A process for the manufacture of N-protected α-aminoketones and N-protected α-aminoalcohols of the formula

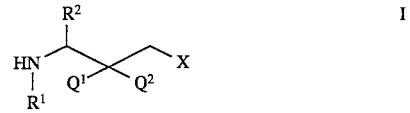

wherein X is halogen, one of $Q^1$ and $Q^2$ is hydrogen and the other is hydroxy or $Q^1$ and $Q^2$ together are oxo, $R^1$ is an amino protecting group and $R^2$ is hydrogen or the characterizing group of an α-aminocarboxylic acid,
starting from the corresponding lower alkyl N-protected α-aminocarboxylates via corresponding lower alkyl N-silyl protected α-aminocarboxylates.

10 Claims, No Drawings

METHOD OF PRODUCING HALOGENATED AND ALPHA-AMINOALCHOHOLS

BACKGROUND OF THE INVENTION

The present invention relates to a novel method of manufacturing halogenated α-aminoketones and α-aminoalcohols of the formula

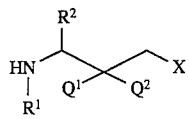

wherein X is halogen; one of $Q^1$ and $Q^2$ is hydrogen and the other is hydroxy, or $Q^1$ and $Q^2$ together are oxo; $R^1$ is an amino protecting group; and $R^2$ is hydrogen or the characterizing group of an α-aminocarboxylic acid.

Generally, the process comprises
a) reacting an ester of formula

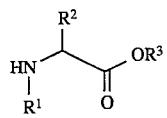

wherein $R^3$ is lower-alkyl, and $R^1$ and $R^2$ are as defined above, with a lower-alkyl-lithium and an organochlorosilane of the formula $ClSi(R^4,R^5,R^6)$, wherein $R^4$, $R^5$ and $R^6$ are each independently selected from lower-alkyl and phenyl, to yield the compound of formula

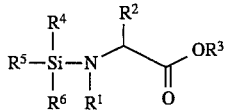

wherein $R^1$–$R^6$ are as defined above; and b) reacting the silyl-protected compound of formula III with dihalogenated methane and a lower-alkyl-lithium to yield a compound for formula I.

The compounds of formula I, which are described e.g. in J. Med. Chem. 1990, 33, 1285–1288 and in European Patent Publication 0 432 695, and, respectively, in U.S. Pat. No. 5,196,438, are valuable intermediates for the manufacture of pharmacologically active compounds, particularly compounds for the treatment of viral infections.

DETAILED DESCRIPTION OF THE INVENTION

The method in accordance with the present invention comprises:

a) reacting an ester of the formula

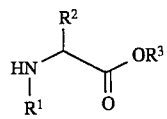

wherein $R^3$ is lower-alkyl, and $R^1$ and $R^2$ are as defined above, with a lower-alkyl-lithium and an organochlorosilane of the formula $ClSi(R^4, R^5, R^6)$, wherein $R^4$, $R^5$ and $R^6$ are each independently selected from lower-alkyl and phenyl, to yield the compound of formula

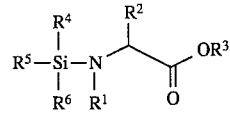

wherein $R^1$ is an amino protecting group; $R^2$ is hydrogen or the characterizing group of an α-aminocarboxylic acid; $R^3$ is lower-alkyl; $R^4$, $R^5$ and $R^6$ are each independently selected from lower-alkyl and phenyl; and b) reacting the silyl-protected compound of formula III with dihalogenated methane and a lower-alkyl-lithium to yield a compound for formula I.

Optionally, the ketone of formula I in which $Q^1$ and $Q^2$ together form an oxo group may be reduced to the corresponding alcohol by methods well known in the art.

As used herein, the following terms have the following meanings.

"Halogen" denotes bromine, chlorine, fluorine or iodine.

"Amino protecting groups" are well known in the art and include lower-alkoxycarbonyl groups, benzyloxycarbonyl, phenoxycarbonyl or 9-fluorenylmethoxycarbonyl, all of which form a protective carbamate with the amino group; or formyl, acetyl or benzoyl which form an amide with the amino group; or allyl or trityl.

A "characterizing group of an α-aminocarboxylic acid" denotes the group $R^2$ in a natural or synthetic α-aminocarboxylic acid of formula $H_2NCH(R^2)COOH$. $R^2$ groups present in natural α-aminocarboxylic acids are methyl (in alanine), isopropyl (valine), sec.butyl (leucine), methylthioethyl (methionine), benzyl (phenylalanine), 3-indolylmethyl (tryptophan), hydroxymethyl (serine), 1-hydroxyethyl (threonine), mercaptomethyl (cysteine), p-hydroxybenzyl (tyrosine), carbamoylmethyl (asparagine), carbamoylethyl (glutamine), 4-aminobutyl (lysine), 3-guanidinopropyl (arginine) and S-imidazolylmethyl (histidine). Cyclohexylmethyl is an example of an $R^2$ group in a synthetic α-aminocarboxylic acid.

"Lower-alkyl" means straight- or branched-chain, saturated hydrocarbon groups with 1–8, preferably 1–4, carbon atoms, such as methyl, ethyl, n-propyl, isopropyl, n-butyl, isobutyl, sec.butyl, tert.butyl, pentyl, hexyl, heptyl or octyl.

"Oxo" as used herein, means that $Q_1$ and $Q_2$ together are an oxygen atom.

In a preferred embodiment of the present invention, the halomethylation of the ester of formula II to the corresponding ketone of formula I in which $Q^1$ and $Q^2$ together are oxo is accomplished by treatment with halogenated methyllithium that is generated in situ. The halogenated methyllithium is conveniently formed using dihalogenated methane, preferably using bromochloromethane, and a lower-alkyl-lithium, preferably butyllithium or hexyllithium, in an ether, preferably tetrahydrofuran, at –20° to –120° C., preferably –80° C.

Unexpectedly, applicants have found that the above-described protection of the amino group in am ester of formula II, which is already protected by the group $R^1$, with a silyl protecting group to form a compound of formula III as an intermediate, results in a considerable increase in yield of compounds of formula I. Moreover, the formation of the silyl-protected intermediate of formula III allows for almost complete conversion of compounds of formula II to compounds of formula I using significantly less lower-alkyl-lithium and dihalogenated methane than would be required if the conversion did not proceed through intermediates of formula III.

Butyllithium or hexyllithium is preferably used as the lower-alkyl-lithium. Chlorotrimethylsilane is preferably used as the organochlorosilane of formula $ClSi(R^4,R^5,R^6)$.

The optional reduction of the resulting halomethyl ketone of formula I is conveniently carried out in a solvent such as toluene, tetrahydrofuran or an alcohol, preferably methanol, ethanol or isopropanol, at a temperature between −30° and 80° C., preferably −15° C. and 50° C., optionally under reduced pressure, using sodium bis(2-methoxyethoxy)aluminum hydride, lithium aluminum hydride, lithium aluminium tri-tert.-butoxyhydride, sodium borohydride, tetramethylammonium borohydride or, preferably, using an aluminum tri-alkoxide or lithium aluminum-tri-alkoxyhydride. The term "alkoxide" as used herein embraces straight- or branched-chain, saturated hydrocarbon oxides with 1–8, preferably 3–4, carbon atoms, namely methyl, ethyl, n-propyl, isopropyl, n-butyl, isobutyl, sec.-butyl and tert.-butyl oxide as well as pentyl, hexyl, heptyl and octyl oxides. The aluminum compounds can have identical or different alkoxide groups. Aluminum-tri-isopropoxide and aluminum-tri-sec.-butoxide are especially preferred compounds. The reagents lithium aluminum- tri-tert.-butoxyhydride, aluminum-tri-isopropoxide and aluminum-tri-sec.-butoxide gave unexpectedly a high stereoselectivity of 95:5 of the (1S,2S) and (1S,2R) isomeric halohydrins of formula I, which in turn can be crystallized from the reaction medium in greater than 99% optical purity.

The ester starting materials of formula II and the corresponding primary amines from which they are derived are known or can be prepared by methods well known in the art and is exemplified in Example 1A.

EXAMPLE 1

A) 160 ml of thionyl chloride were added dropwise to 800 ml of methanol at 0° C. Subsequently, the mixture was treated with 330.4 g of L-phenylalamine and heated to 45° C. for 2.5 hours. The resulting solution was concentrated completely, the residue was taken up in 1.6 l of water and treated at 0° C. with 185 ml of methyl chloroformate while holding the pit between 6–7 with 40% sodium hydroxide solution. The solution was extracted with toluene and the extracts, after washing with water, were concentrated and the residue was dried at 45° C./0.1 mbar, yielding 474.6 g (100%) of pure methyl (S)-2-methoxycarbonylamino-3-phenyl-propionate. IR (KBr): 3338m (NH), 1726s hr. (C=O), 1531s (amide II).

B) 41.7 ml of a 2.6 molar solution of hexyllithium in hexane were added dropwise at −80° C. to a solution of 9.50 g of methyl (S)-2-methoxycarbonylamino- 3-phenyl-propionate and 3.22 ml of bromochloromethane in 60 ml of tetrahydrofuran. Subsequently, a further 2.14 ml of bromochloromethane were added and the mixture was again treated with 23 ml of hexyllithium solution, a further 1.54 ml of bromochloromethane were added and the mixture was again treated with 7.7 ml of hexyllithium solution. The solution was treated at −80° C. with 15 ml of 20% methanolic hydrochloric acid, warmed to 22° and diluted with 100 ml of water and 40 ml of tetrahydrofuran. The phases were separated, the organic phase was washed with saturated sodium chloride solution, dried and concentrated. The residue was recrystallized from 40 ml of ethyl acetate and 160 ml of hexane and the crystallizate was dried, yielding 3.83 g (37%) of pure methyl (S)-(1-benzyl-3-chloro- 2-oxo-propyl)-carbamate, m.p. 121°–122° C. IR (KBr): 3336s (NH), 1737s and 1686s (C=O), 1535s (amide II).

C) 15.4 ml of a 2.6 molar solution of hexyllithium in hexane were added dropwise at −80° C. to a solution of 9.50 g of methyl (S)-2-methoxycarbonylamino- 3-phenyl-propionate in 60 ml of tetrahydrofuran. Subsequently, the mixture was treated with 5.60 ml of chlorotrimethylsilane. The resulting suspension was stirred and treated with 3.22 ml of bromochloromethane. Subsequently, 18.4 ml of hexyllithium solution were added. The solution was treated at −80° C. with 11 ml of 20% methanolic hydrochloric acid, warmed to 22° and diluted with 100 ml of water and 40 ml of tetrahydrofuran. The phases were separated and the organic phase was washed with saturated sodium chloride solution, dried and concentrated. The residue was recrystallized from ethyl acetate and hexane and the crystallizate was dried, yielding 7.20 g (70%) of pure methyl (S)-( 1-benzyl-3-chloro-2-oxo-propyl)carbamate, m.p. 122°–123° C. IR (KBr): 3336s (NH), 1737s and 1686s (C=O), 1535s (amide II).

D) Reduction Reactions a) 33.06 g of lithium aluminum tri-tert.-butoxyhydride were added portionwise at −15° C. to a suspension of 25.57 g of methyl (S)( 1-benzyl-3-chloro-2-oxo-propyl)-carbamate in 280 ml of ethanol and the mixture was subsequently hydrolyzed at 0° C. with 140 ml of 3N hydrochloric acid and 170 ml of water. The suspension was concentrated to 370 ml, filtered and the residue was washed with water/ethanol (4:1) and dried, yielding 23.27 g (90%) of isomerically-pure methyl ( 1S,2S)-( 1-benzyl-3-chloro-2-hydroxy- propyl)-carbamate, m.p. 163°–164.5° C. IR (KBr): 3323s, br. (NH, OH), 1689 (C=O), 1546s (amide II).

b) 25.57 g of methyl (S)-( 1-benzyl-3-chloro-2-oxo-propyl)carbamate were added portionwise at 22° C. to a suspension of 21.44 g of aluminum isopropoxide in 260 ml of isopropanol. The suspension was stirred at 50° C./400 mbar for 2 hours, hydrolyzed at 0° C. with 100 ml of 3N hydrochloric acid, subsequently concentrated to a volume of 125 ml, diluted with 125 ml of water, cooled to 0° C. and filtered. The residue was washed with water/isopropanol (4:1) and dried, yielding 23.01 g (89%) of isomerically-pure methyl ( 1S,2S)-( 1-benzyl-3-chloro-2-hydroxypropyl)-carbamate, m.p. 162°–163.5° C. IR (KBr): 3323s, br. (NH, OH), 1689 (C=O), 1546s ( amide II).

c) 3.75 g of sodium borohydride were added portionwise at −15° C. to a suspension of 46.03 g of methyl (S)-(1-benzyl-3-chloro- 2-oxo-propyl)-carbamate in 275 ml of methanol. The mixture was stirred for 1.5 hours, diluted with 21 ml of acetic acid and 460 ml of water, stirred at −15° C. for 1 hour and filtered. The residue was washed with water, recrystallized from 430 ml of isopropanol and the crystallizate was dried, yielding 28.68 g (62%) of a 98:2 mixture of the ( 1S,2S):( 1S,2R)-isomers of methyl ( 1-benzyl-3-chloro-2 -hydroxy-propyl)-carbamate, m.p. 161.5°–162.5° C. IR (KBr): 3323s, hr. (NH, OH), 1689s (C=O), 1546s (amide II).

EXAMPLE 2

A) In a manner analogous to Example 1A, from 50.8 g of L-leucine methyl ester hydrochloride were obtained 55.3 g (97%) of methyl (S)-2-methoxycarbonylamino-4-methyl-valerate, IR ( film): 3341m (NH), 1727s br. (C=O), 1533s (amide II).

B) Also, in a manner analogous to Example 1C, from 20.3 g of methyl (S)-2-methoxycarbonylamino-4-methyl-valerate were obtained 15.5 g (70%) of methyl (S)-( 1-isobutyl-3-chloro-2-oxopropyl)-carbamate after crystallization from diisopropyl ether/hexane, m.p. 41°–42° C., IR (KBr): 3321s (NH), 1739s and 1686s (C=O), 1534s (amide II).

C) In a manner analogous to Example 1D, from 4.03 g of methyl (S)-(1-isobutyl-3-chloro-2-oxo-propyl)-carbamate were obtained 2.32 g (S7%) of methyl (1S,2S)-(1-isobutyl-3-chloro-2-hydroxypropyl)-carbamate, m.p. 77°–79° C., IR (KBr): 3316s, hr. (NH, OH), 1690s (C=O), 1549s (amide II).

EXAMPLE 3

A) In a manner analogous to Example 1A, from 149 g of L-methionine were obtained 221 g (100%) of methyl (S)-2-methoxycarbonylamino-4-methylthiobutyrate.

B) In a manner analogous to Example 1C, from 22.1 g of methyl (S)-2-methoxycarbonylamino-4-methylthiobutyrate were obtained 16.8 g (70%) of methyl (S)-(3-chloro-1-methylthioethyl-2-oxopropyl)carbamate.

C) In a manner analogous to Example 1D, from 24.0 g of methyl (S)-(3-chloro-1-methylthioethyl-2-oxopropyl)carbamate were obtained 20.5 g (85%) of methyl (1S,2S)-(3-chloro-2-hydroxy-1-methylthioethyl-propyl)carbamate.

EXAMPLE 4

A) In a manner analogous to Example 1A, from 50.0 g of L-serine methyl ester hydrochloride were are obtained 50.9 g (89%) of methyl (S)-3-hydroxy-2-methoxycarbonylamino-propionate, IR (film): 3380m, hr. (NH, OH), 1722s, hr. (C=O), 1534s (amide II).

B) From 19.9 g of methyl (S)-3-hydroxy-2-methoxycarbonylamino-propionate, and using a method analogous to Example 1C utilizing double the amount of hexyllithium and chlorotrimethylsilane for the protection of the NH and OH groups, were obtained 5.3 g (33%) of pure methyl (S)-(3-chloro-1-hydroxymethyl-2-oxopropyl)-carbamate after chromatography on silica gel with hexane/tetrahydrofuran/methanol (5:1:1), IR (film): 3389s, hr. (NH, OH), 1706s, br. (C=O), 1529s (amide II).

C) In a manner annalogous to Example 1D, from 2.6 g of methyl (S)-(3-chloro-1-hydroxymethyl-2-oxo-propyl)-carbamate were obtained 1.71 g (73%) of methyl (1S,2S)-(3-chloro-2-hydroxy-1-hydroxymethyl-propyl)-carbamate after extraction with ethyl acetate, IR (film): 3388s, hr. (NH, OH), 1705s (C=O), 1529s (amide II).

I claim:

1. A method for the manufacture of halogenated aminoketones and α-aminoalcohols of the formula

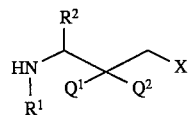

wherein X is halogen; one of $Q^1$ and $Q^2$ is hydrogen and the other is hydroxy, or $Q^1$ and $Q^2$ together are oxo; $R^1$ is an amino protecting group; and $R^2$ is hydrogen or the characterizing group of an α-aminocarboxylic acid, which process comprises a) reacting an ester of the formula

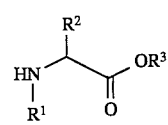

wherein $R^3$ is lower-alkyl and $R^1$ and $R^2$ are as defined above, with a lower-alkyl-lithium and an organochlorosilane of the formula $ClSi(R^4,R^5,R^6)$, wherein $R^4$, $R^5$ and $R^6$ are each independently selected from lower-alkyl and phenyl, to yield the compound of formula

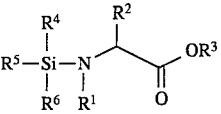

wherein $R^1$ through $R^6$ are as defined above; and b) reacting the silyl-protected compound of formula III with dihalogenated methane and a lower-alkyl-lithium to yield a compound for formula I.

2. The method of claim 1 wherein the ketone of formula I in which $Q^1$ and $Q^2$ together are oxo is reduced to the corresponding alcohol.

3. The method of claim 1, wherein the ester of formula II, $R^1$ and $R^3$ are methyl.

4. The method of claim 1, wherein in the organochlorosilane of the formula $ClSi(R^4,R^5,R^6)$, $R^4$, $R^5$, and $R^6$ are methyl.

5. The method of claim 1, wherein bromochloromethane is used as the dihalogenated methane.

6. The method of claim 1, wherein the lower-alkyl-lithium is selected from butyllithium and hexyllithium.

7. The method of claim 1, wherein the organochlorosilane of the formula $ClSi(R^4, R^5,R^6)$ is chlorotrimethylsilane.

8. The method of claim 2, wherein an aluminum trialkoxide or lithium aluminum trialkoxyhydride is used as the reducing agent.

9. The method of claim 8, wherein the reducing agent is selected from aluminum-tri-isopropoxide, aluminum-tri-sec.butoxide, and lithium aluminum-tri-tert.-butoxyhydride.

10. A method for the manufacture of halogenated α-aminoketones and α-aminoalcohols comprising a) reacting an ester of formula

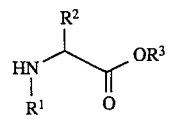

wherein $R^1$ is an amino protecting group; $R^2$ is hydrogen or the characterizing group of an α-aminocarboxylic acid; and $R^3$ is lower-alkyl, with a lower-alkyl-lithium and an organochlorosilane of the formula $ClSi(R^4,R^5, R^6)$, wherein $R^4$, $R^5$. and $R^6$ are each independently selected from lower-alkyl and penyl; and b) reacting the compound formed in step a) with the dihalogenated methane and lower-alkyl-lithium to yield a compound of the formula

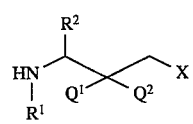

wherein $R^1$–$R^6$ are as defined above.

* * * * *